(12) United States Patent
Niwa et al.

(10) Patent No.: US 7,850,605 B2
(45) Date of Patent: Dec. 14, 2010

(54) INSERTING SHAPE DETECTING PROBE

(75) Inventors: Hiroshi Niwa, Koganei (JP); Chieko Aizawa, Hachioji (JP); Fumiyuki Onoda, Tama (JP)

(73) Assignee: Olympus Corporation, Tokyo (JP)

( * ) Notice: Subject to any disclaimer, the term of this patent is extended or adjusted under 35 U.S.C. 154(b) by 921 days.

(21) Appl. No.: 10/951,101

(22) Filed: Sep. 27, 2004

(65) Prior Publication Data

US 2005/0070790 A1    Mar. 31, 2005

(30) Foreign Application Priority Data

Sep. 30, 2003 (JP) ............... 2003-342418
Sep. 30, 2003 (JP) ............... 2003-342421

(51) Int. Cl.
*A61B 1/00* (2006.01)
*A61B 1/04* (2006.01)
*A61M 25/00* (2006.01)

(52) U.S. Cl. ............... 600/145; 600/117; 600/434
(58) Field of Classification Search ............... 600/117, 600/139, 145, 434–435
See application file for complete search history.

(56) References Cited

U.S. PATENT DOCUMENTS

| | | | | |
|---|---|---|---|---|
| 4,301,790 A | * | 11/1981 | Bol et al. ............... | 600/109 |
| 4,313,431 A | * | 2/1982 | Frank ............... | 600/108 |
| 5,482,029 A | * | 1/1996 | Sekiguchi et al. ............... | 600/109 |
| 5,840,024 A | | 11/1998 | Taniguchi et al. | |
| 5,910,104 A | * | 6/1999 | Dobak et al. ............... | 600/121 |
| 6,059,718 A | * | 5/2000 | Taniguchi et al. ............... | 600/117 |
| 6,304,769 B1 | | 10/2001 | Arenson et al. | |
| 2002/0052546 A1 | | 5/2002 | Frantz et al. | |
| 2003/0028096 A1 | * | 2/2003 | Niwa et al. ............... | 600/424 |

FOREIGN PATENT DOCUMENTS

| | | |
|---|---|---|
| JP | 05-244690 | 9/1993 |
| JP | 11-076154 | 3/1999 |
| JP | 11-340616 | 12/1999 |
| JP | 2002-043730 | 2/2002 |
| JP | 2002-345732 | 12/2002 |
| JP | 2003-47586 | 2/2003 |

* cited by examiner

*Primary Examiner*—Philip R Smith
(74) *Attorney, Agent, or Firm*—Scully, Scott, Murphy & Presser, P.C.

(57) ABSTRACT

An inserting shape detecting probe has a long and slender core wire, a plurality of shape detecting devices, signal lines, and an outer sheath. The plurality of shape detecting devices extended from the signal lines are fixed to the core wire at a predetermined interval. The core wire is inserted in the outer sheath. The inserting shape detecting probe has a thermal radiating member which is arranged along the outer circumference of at least one of the shape detecting devices.

8 Claims, 12 Drawing Sheets

INSERTING SHAPE DETECTING PROBE

This application claims benefit of Japanese Applications No. 2003-342421 filed on Sep. 30, 2003 and No. 2003-342418 filed on Sep. 30, 2003, the contents of which are incorporated by this reference.

BACKGROUND OF THE INVENTION

1. Field of the Invention

The present invention relates to an inserting shape detecting probe, and more particularly, to an inserting shape detecting probe which detects the inserting shape of an endoscope inserting portion by inserting the inserting shape detecting probe in a treatment tool inserting channel or by fixing the inserting shape detecting probe in an inserting portion of the endoscope.

2. Description of the Related Art

Recently, an endoscope is widely used in the medical field and the industrial field. Particularly, in the endoscope used in the medical field, by inserting a soft inserting portion to the winding body cavity, the organ at the deep portion in the body cavity is observed or diagnosed without the incision of the body surface, or medical and therapeutic treatment such as the removal of the lesion organ in the body cavity or the resection of the polyp are performed by inserting a treatment tool in a treatment tool inserting channel which is arranged to the endoscope if necessary.

However, when the endoscope having an elongated inserting portion is inserted from the anus side and then examines the digestive tract on the bottom side, the smooth insertion of the inserting portion in the winding body cavity needs the skill. Because it is not determined where the distal end position of the inserting portion exists in the body cavity and how the inserting portion is inserted.

Then, in order to know the inserting state of the inserting portion of the endoscope, an X-ray non-transmitting portion is arranged to the inserting portion, and the inserting shape of the endoscope is obtained by the sight through the X-ray, and thus the bending state of the inserting portion or the distal end position of the inserting portion is detected. However, an endoscope shape detecting device using the X-ray is large in scale, and an examination room needs a sufficiently wide space to arrange a device for irradiating the X-ray.

Further, an operator must operate the endoscope in addition to the operation for irradiating the X-ray, in the endoscope examination. Thus, the burden of the operator increases. It is not preferable to detect the inserting state of the endoscope inserting portion with the X-ray.

Herein, the inserting portion of the endoscope has a plurality of devices for transmitting electromagnetic waves or ultrasonic waves, an external detecting device receives signals from the transmitting devices of the inserting portion, the shape of the inserting portion is displayed on the screen of the detecting device upon inserting the inserting portion of the endoscope. Further, the endoscope comprises a treatment tool inserting channel comprising an inserting shape detecting probe inserted therein comprising a magnetic field detecting device arranged in the treatment tool inserting channel. Then, the inserting portion is inserted in the body cavity in the inserting state of the inserting shape detecting probe, and thus the shape of the inserting portion is displayed on the screen of the detecting device upon inserting the inserting portion of the endoscope.

As mentioned above, the inserting shape detecting probe has therein the plurality of shape detecting devices and a plurality of signal lines. Upon using the inserting shape detecting probe, an electric signal from the inserting shape detecting device is applied to the inserting shape detecting probes via the plurality of signal lines, and the inserting shape detecting probe is driven. In this case, the inserting shape detecting probes might be heated.

Generally, "IEC60601-2-18: Particular requirements for the safety of endoscopic equipment" prescribed by IEC (International Electrotechnical Commission) is applied to an endoscope apparatus. In the requirements, "Surface temperature of attaching portion" (42.3 section) is applied to the increase of surface temperature of the inserting shape detecting probe.

Conventionally, in the endoscope apparatus in which the inserting shape detecting probe is inserted in the treatment tool inserting channel of the inserting portion and the shape of the endoscope inserting portion is detected, the inserting shape detecting probe comprises a plurality of shape detecting devices and a plurality of signal lines for the purpose of the precise detection.

FIG. 15 is an enlarged cross-sectional view of a main portion showing a part of one conventional inserting shape detecting probe having the plurality of shape detecting device and the plurality of signal lines extended from the shape detecting devices.

Referring to FIG. 15, the one conventional inserting shape detecting probe has a plurality of source coils 121 (only one is shown in FIG. 15) as shape detecting devices on a core wire 123 at a predetermined interval. Further, the source coil 121 and a signal line 126 extended therefrom are arranged in an outer sheath 120 and, then, the outer sheath 120 is filled with a solvent (not shown) such as silicone, thereby forming the inserting shape detecting probe.

However, the conventional inserting shape detecting probe with the above-mentioned structure is manufactured with the troublesomeness for a long time. Further, the arrangement position of the signal lines are not uniform upon filling the solvent. The inserting shape detecting probe with the desired specification is not assembled.

Then, Japanese Unexamined Patent Application Publication No. 2003-47586, for example, discloses another inserting shape detecting probe which is inserted in the treatment tool inserting channel and the shape of the inserting portion is detected with high precision, high-assembling property, and high-resistant property.

As disclosed in Japanese Unexamined Patent Application Publication No. 2003-47586, the other inserting shape detecting probe comprises: a long and slender core wire having a plurality of shape detecting devices fixed thereto at a predetermined interval, from which a plurality of signal lines are extended; a plurality of inner sheaths which are arranged on the proximal end portion side of the shape detecting devices that is fixed to the core wire and in which the core wire and the signal lines are inserted; connecting and fixing means which covers the shape detecting devices and the inner sheaths adjacent to the shape detecting device and which integrally connects them; and an outer sheath in which the plurality of shape detecting devices integrated to the core wire and the plurality of inner sheaths are inserted. By inserting the inserting shape detecting probe in the treatment tool inserting channel of the endoscope, the shape of the inserting portion in the endoscope is precisely detected.

FIGS. 16 and 17 are diagrams showing the other conventional inserting shape detecting probe, which is disclosed in Japanese Unexamined Patent Application Publication No. 2003-47586. FIG. 16 is a diagram showing the entire structure of the other inserting shape detecting probe. FIG. 17 is an enlarged cross-sectional view showing a part of the other inserting shape detecting probe shown in FIG. 16.

Referring to FIGS. 16 and 17, an inserting shape detecting probe 101 comprises; a long and slender core wire 123 having a plurality of source coils 121A to 121L fixed thereto at a predetermined interval, from which signal lines 126 are extended; a plurality of inner sheaths 124, which are arranged on the side of the proximal end portions of the source coils 121A to 121L fixed to the core wire 123 and which have the core wire 123 and the signal line 126 inserted therein; a connecting and fixing member (thermal contracting tube or adhesive layer) which covers the source coils 121A to 121L and the inner sheaths 124 adjacent thereto and which is integrally connected to the source coils 121A to 121L; an outer sheath 120 having the plurality of source coils 121A to 121L integrally arranged to the core wire 123 and the plurality of inner sheaths 124 inserted therein.

In the other inserting shape detecting probe shown in FIGS. 16 and 17, the inserting shape detecting probe is inserted in the treatment tool inserting channel and the shape of the inserting portion is precisely detected. Further, the inserting shape detecting probe is realized with high assembling-property and resistant property.

SUMMARY OF THE INVENTION

According to the present invention, an inserting shape detecting probe comprises an outer sheath, a long and slender core wire, a plurality of shape detecting devices, and signal lines. The core wire is inserted in the outer sheath, the plurality of shape detecting devices are fixed to the core wire at a predetermined interval, and the signal lines are extended from the plurality of shape detecting devices. The inserting shape detecting probe comprises: a thermal radiating member which is arranged along the outer circumference of at least one of the shape detecting devices.

Other features and advantages of the present invention will be fully apparent from the following description.

DESCRIPTION OF THE PREFERRED EMBODIMENTS

Figure 1:
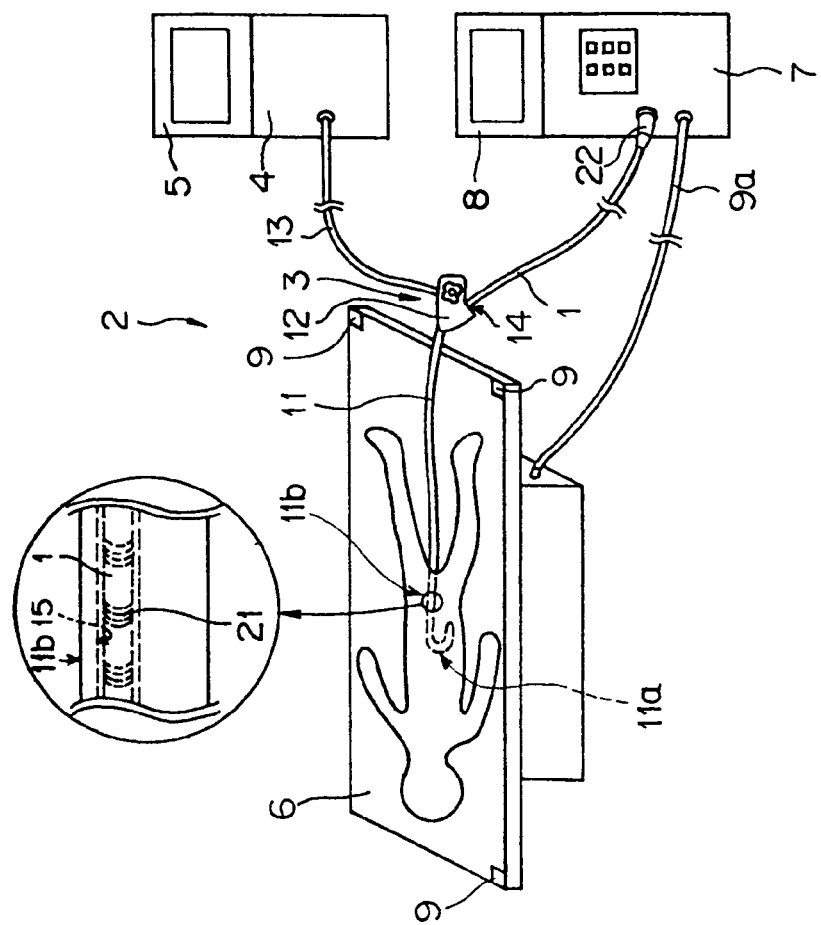
FIG. 1 is a diagram showing the schematic structure of an inserting shape detecting device using an inserting shape detecting probe according to a first embodiment of the present invention.

Before describing the detail of an inserting shape detecting probe according to a first embodiment of the present invention, first, a description is given of the schematic structure of an endoscope apparatus using the inserting shape detecting probe with reference to FIG. 1.

Referring to FIG. 1, according to the first embodiment, an endoscope apparatus 2 using an inserting shape detecting probe 1 mainly comprises: an endoscope 3 which is inserted from the anus in the body cavity of the body to be examined and which observes an observing portion; a video processor 4 which generates a video signal from an image pick-up signal obtained by picking-up an image with the endoscope 3; a monitor 5 which displays the video signal from the video processor 4 as an endoscope image; a bed 6 for detecting the inserting shape, on which the specimen lies down and which detects the magnetic field from the inserting shape detecting probe 1; an inserting shape detecting device 7 which drives the inserting shape detecting probe 1 and outputs a video signal which images the inserting shape of the endoscope 3 in the body cavity based on a signal corresponding to the magnetic field detected by the bed 6 for detecting the inserting shape; and a monitor 8 which displays the inserting portion shape outputted from the inserting shape detecting device 7.

The endoscope 3 comprises: an elongated inserting portion 11 inserted in the body cavity comprising an inserting portion bending portion 11a which is on the distal end side and is bent with a small curvature radius, and an inserting portion flexible line portion 11b which is on the proximal end side rather than the inserting portion bending portion 11a, which is bent with a relatively large curvature radius; an operating portion 12 having a function of a grip portion continuously arranged on the proximal end side of the inserting portion 11; and a universal cord 13 which is extended from the side portion of the operating portion 12 and which is connected to an external device such as the video processor 4.

The inserting shape detecting probe 1 is inserted in a treatment tool inserting channel 15 from a treatment tool inserting port 14 arranged to the operating portion 12 of the endoscope 3. A plurality of source coils 21 as shape detecting devices for generating the magnetic field are arranged to the inserting shape detecting probe 1 (refer to FIG. 2 in detail). The inserting shape detecting probe 1 is connected to the inserting shape detecting device 7 via a connector portion 22 arranged to its proximal end portion.

A plurality of sense coils 9 as magnetic field detecting devices are arranged to the bed 6 for detecting the inserting shape so as to detect the magnetic field generated in the source coils 21. The bed 6 for detecting the inserting shape is connected to the inserting shape detecting device 7 via a cable 9*a*. Therefore, detecting signals of the sense coils 9 are transmitted to the inserting shape detecting device 7 via the cable 9*a*.

The inserting shape detecting device 7 comprises: a source coil driving unit (not shown) for driving the source coils 21; a source coil position analyzing unit (not shown) for analyzing the three-dimensional positional coordinates of the source coils 21 based on the signals transmitted from the sense coils 9; and an inserting shape image generating unit (not shown) for calculating the three-dimensional shape of the inserting portion 11, converting the calculated coordinates into the two-dimensional coordinates for the monitor display operation, and imaging the converted data.

According to the first embodiment, the inserting shape-detecting probe 1 comprises the plurality of shape detecting devices for generating the magnetic filed (source coils 21), and the bed 6 for detecting the inserting shape comprises the plurality of magnetic field detecting devices (sense coils 9). However, the present invention is not limited to this and, for example, the inserting shape detecting probe 1 may comprise a plurality of shape detecting device for detecting the magnetic field (sense coils) and the bed 6 for detecting the inserting shape may have a plurality of magnetic field generating devices (source coils).

Next, a description is given of the detailed structure of the inserting shape detecting probe 1 with reference to FIGS. 2 to 9.

Figure 2:
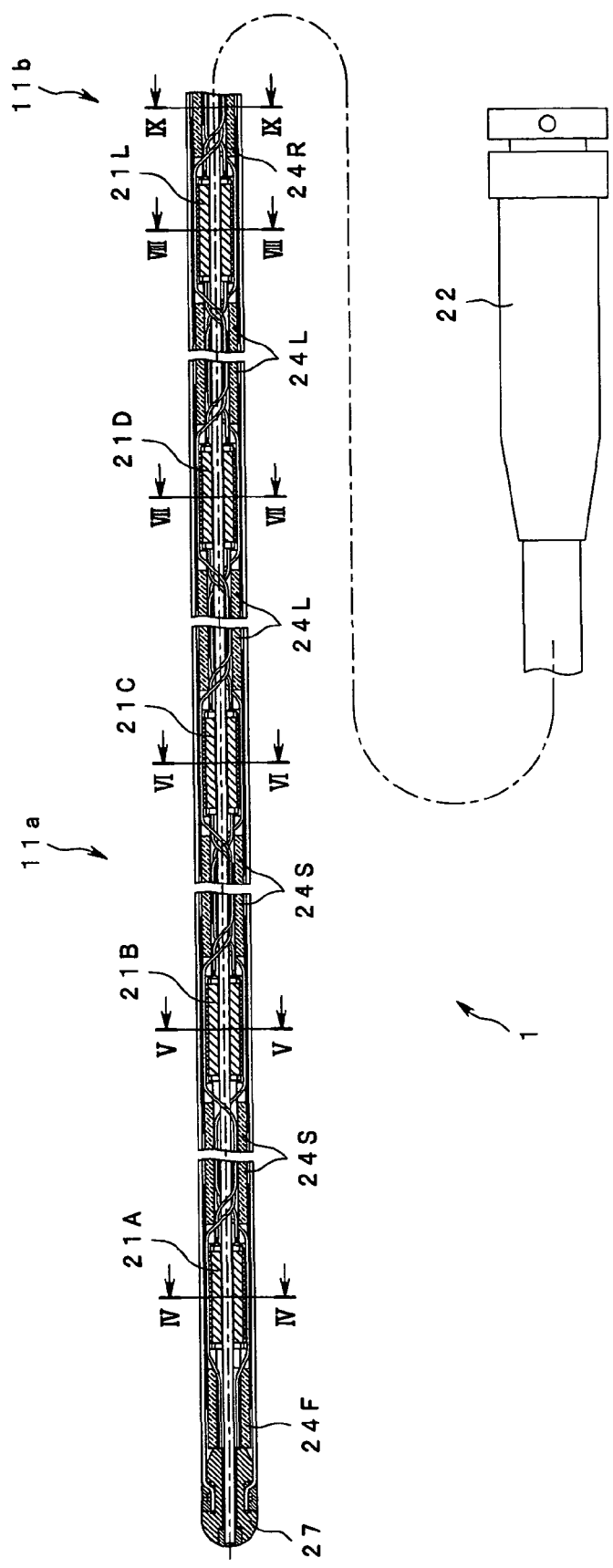
FIG. 2 is a cross-sectional view schematically showing the internal structure of the inserting shape detecting probe shown in FIG. 1.
Figure 3:
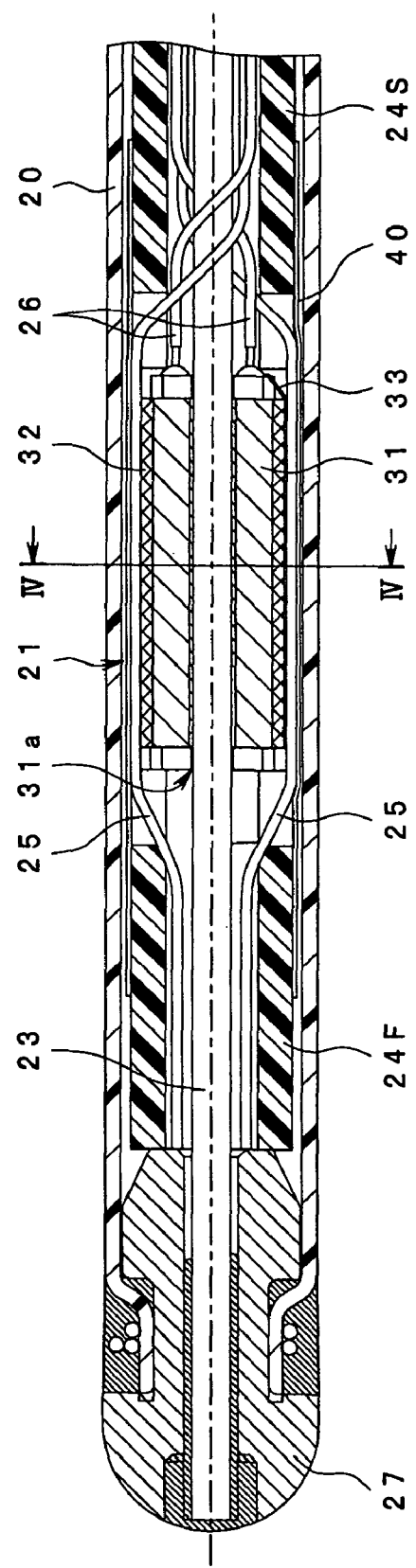
FIG. 3 is an enlarged cross-sectional view of a main portion near a distal end portion of the inserting shape detecting probe shown in FIG. 1.

Referring to FIGS. 2 and 3, the inserting shape detecting probe 1 mainly comprises: an outer sheath 20 which is inserted in the treatment tool inserting channel 15 and which forms its exterior portion; a plurality of source coils 21A to 21L which are cylindrically formed with a hollow portion; a long and slender core wire 23 which is adhered and fixed to the source coils 21A to 21L; inner sheaths (24F, 24S, and 24R, refer to FIG. 2, which will be described in detail later) which are pipe-shaped and are serially arranged to the source coils 21A to 21L; a plurality of thermal radiating members 25 which are arranged within a predetermined area toward the proximal end side from a predetermined portion on the distal end side of the inserting shape detecting probe 1 and which are arranged along the outer circumference of the core wire 23, and the source coils 21A, 21B, and 21C; and a thermal contracting tube 40, as a connecting and fixing member, which covers the source coils 21A to 21L and the inner sheaths 24 adjacent thereto and which integrally connects the source coils 21A to 21L and the inner sheath 24.

Referring to FIG. 2, the source coils 21A to 21L and the inner sheath 24 are alternately arranged to the source coil 21A, the inner sheath 24, the source coil 21B, the inner sheath 24, the source coil 21C, . . . , toward the proximal end portion from the distal end portion side of the inserting shape detecting probe 1.

Further, as mentioned above, the thermal contracting tube 40 is arranged between the source coils 21A to 21L and the inner sheaths 24 adjacent thereto. The thermal contracting tube 40 covers the source coils 21A to 21L, and are arranged to cover both end portions of the inner sheaths 24. Thus, the source coils 21A to 21L are integrally connected to the inner sheaths 24.

In the inserting shape detecting probe 1 according to the first embodiment, the number of source coils 21 is twelve. The source coil on the distal end side is a first source coil 21A, and the subsequent source coils are second to twelfth source coils 21B to 21L.

Signal lines 26 are connected to one-end portions of the source coils 21A to 21L. The signal lines 26 transmit driving signals from the source coil driving unit (not shown) of the inserting shape detecting device 7. Therefore, the signal lines 26 extended from the source coils 21A to 21L are assumed as the signal lines 26A to 26L. In other words, reference symbol 26A denote the signal line extended from the source coil 21A, and reference symbols 26B to 26L denote the signal lines extended from the source coils 21B to 21L, respectively, similarly (refer to FIGS. 4 to 9).

The signal lines 26A to 26L are inserted in the inner sheaths 24 which are arranged on the side of the proximal end portions of the source coils 21A to 21L, and are extended to the side of the proximal end along the outer circumference of the source coils 26A to 26L arranged thereamong. Further, the signal lines 26A to 26L are inserted in the thermal contracting tube 40.

That is, the signal lines 26A to 26L extended from the source coils 21A to 21L are inserted in the inner sheaths 24 on the side of the proximal ends of the source coils 21B to 21L. Then, the signal lines 26A to 26L are inserted in the thermal contracting tube 40 along the outer side surfaces of the source coils 21B to 21L adjacent thereto. Further, the signal lines 26A to 26L are inserted in the inner sheaths 24 again and the entire signal lines 26A to 26L are finally extended to the connector portion 22 on the side of the proximal end of the inserting shape detecting probe 1. As the inner sheath 24 is closer to the proximal end of the inserting shape detecting probe 1, a larger number of signal lines are inserted. A large number of signal lines 26 are along the source coils 21A to 21L which are closer to the proximal end of the inserting shape detecting probe 1 (refer to FIG. 8). The source coils 21A to 21L, the signal lines 26A to 26L, and the inner sheath 24*s* are inserted in the outer sheath 20.

The signal lines 26A to 26L are wound to the outer circumference of the core wire 23 so as to generate predetermined loose along the core wire 23 in the inner sheaths 24. Because upon bending the inserting shape detecting probe 1 and the tension is applied to the signal lines 26A to 26L, the damage such as the short circuit is prevented.

The source coils 21A to 21L are adhered and are fixed to the core wire 23 at predetermined positions at a predetermined interval with an adhesive. In this case, the arrangement of the source coils 21A to 21L is as shown in FIG. 2.

The source coils 21A to 21C are arranged to the inserting portion bending portion 11*a* (refer to FIG. 1). In this case, the source coils 21A to 21C function as the devices for detecting the shape of the bending portion, which obtain the shape data of the inserting portion bending portion 11*a*. Further, the source coils 21D to 21L are arranged to the inserting portion flexible line portion 11*b* (refer to FIG. 1). In this case, the source coils 21D to 21L function as devices for detecting the shape of the bending portion, which obtain the shape data of the inserting portion flexible line portion 11b.

Referring to FIG. 3, each of the source coils 21A to 21L mainly comprises: a hollow core member 31 having a through-hole 31a which is pierced through them in the axial direction; a winding 32 which is wound to the outer circumference of the hollow core member 31 and contains an enamel line or the like; and a donut-shaped substrate 33 which is arranged on an end surface of the hollow core member 31. Both end portions of the winding 32 are electrically connected to a substrate 33 by soldering or the like. A pair of signal lines 26 are electrically connected by soldering. Thus, the pair of signal lines 26 are extended from one-end surface sides of the source coils 21A to 21L.

Generally, the signal lines 26A to 26L contain a conductive metallic member such as copper. The metal such as copper has preferable thermal conductivity and therefore the signal lines 26A to 26L have preferable thermal conductivity.

Among the twelve source coils 21A to 21L, the device pitch between the source coils 21A to 21C arranged to the inserting portion bending portion 11a are different from the device pitch between the source coils 21D to 21L arranged to the inserting portion flexible line portion 11b.

Specifically, the arrangement pitch between the source coils 21A to 21C is set to, e.g., 30 [mm]. The arrangement pitch between the source coils 21D to 21L is set to, e.g., 100 [mm].

Among the plurality of inner sheaths 24, reference symbol 24S denotes the inner sheaths (having the pitch of 30 [mm]), which are serially arranged on the side of the proximal ends of the source coils 21A and 21B. Reference symbol 24L denotes the inner sheaths (having the pitch of 100 [mm]), which are serially arranged on the side of the proximal ends of the source coils 21C to 21K. Reference symbol 24R denotes the inner sheaths which are serially arranged on the side of the proximal ends of the source coil 21L (refer to FIG. 2). Reference symbol 24F denotes the inner sheaths which are serially arranged on the side of the distal end portion of the source coil 21A (refer to FIG. 2). Incidentally, the inner sheaths 24R and 24F arranged on both end portions further have a function for applying the strong elasticity to the distal end portion of the outer sheath 20.

The thermal radiating members 25 contain a line member, such as copper, with preferable thermal conductivity and the thermal radiating advantage.

According to the first embodiment, six thermal radiating members 25 are arranged within a predetermined area from a predetermined position on the distal end side of the inserting shape detecting probe 1 to the proximal end side thereof, namely, along the outer circumference of the core wire 23 and the source coils 21A, 21B, and 21C at a predetermined position within the arrangement area of the source coils 21A to 21C from the distal end portion of the inserting shape detecting probe 1 (refer to FIGS. 4 to 9).

In this case, referring to FIGS. 4 to 9, the six thermal radiating members 25 are arranged at the predetermined positions at a predetermined interval on the outer circumferences of the source coils 21A to 21C.

Figure 4:
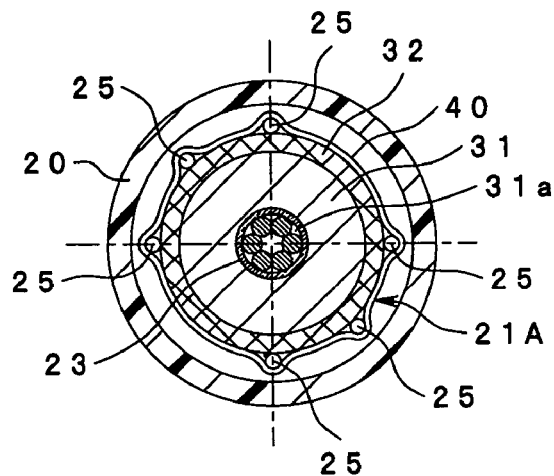
FIG. 4 is a cross-sectional view along a IV-IV line in FIGS. 2 and 3.
Figure 5:
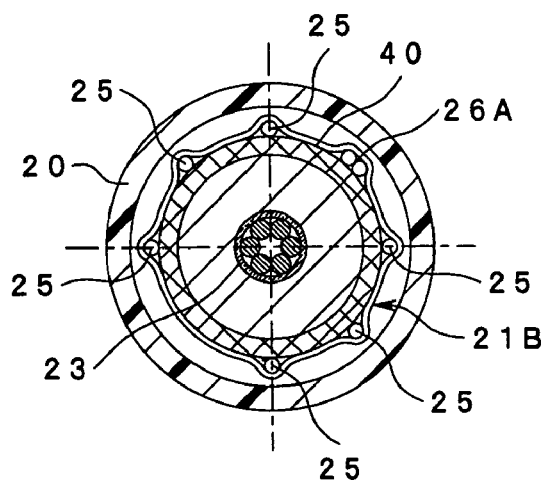
FIG. 5 is a cross-sectional view along a V-V line shown in FIG. 2.
Figure 6:
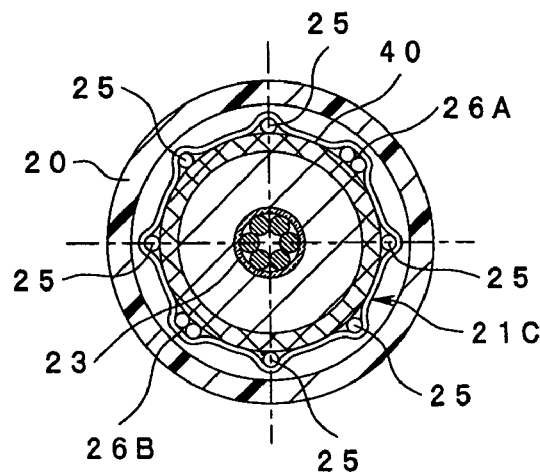
FIG. 6 is a cross-sectional view along a VI-VI line shown in FIG. 2.
Figure 7:
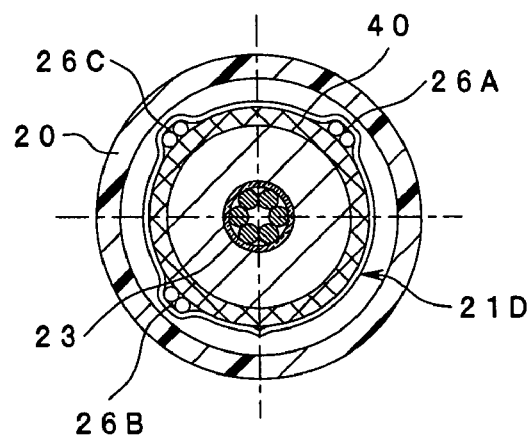
FIG. 7 is a cross-sectional view along a VII-VII line shown in FIG. 2.
Figure 8:
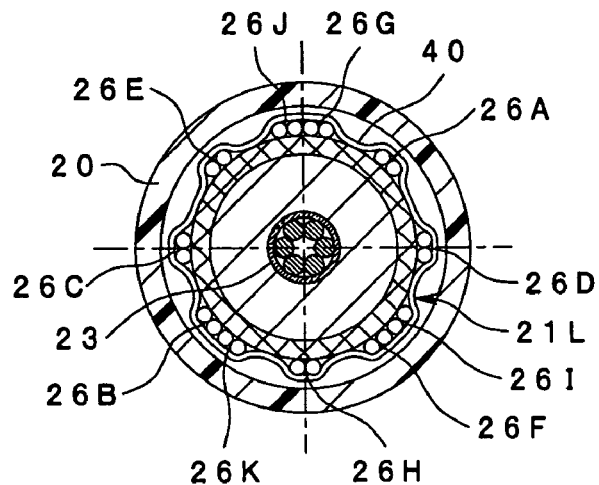
FIG. 8 is a cross-sectional view along a VIII-VIII line shown in FIG. 2.
Figure 9:
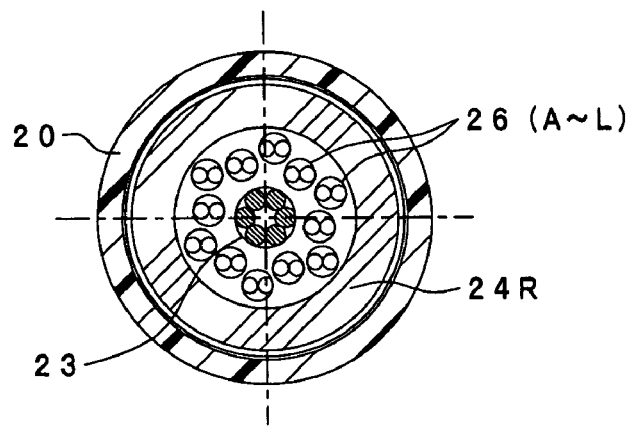
FIG. 9 is a cross-sectional view along a IX-IX line shown in FIG. 2.

Specifically, only the six thermal radiating members 25 are arranged at the predetermined positions on the outer circumference of the source coil 21A in the state shown in FIG. 4. On the outer circumference of the source coil 21B, the six thermal radiating members 25 and the signal line 26A of the source coil 21A are at predetermined positions in the state shown in FIG. 5. On the outer circumference of the source coil 21C, the six thermal radiating members 25 and the signal lines 26A and 26B of the source coils 21A and 21B are at predetermined positions in the state shown in FIG. 6. In the area behind the source coil 21D, the thermal radiating member 25 is not arranged and only the plurality of signal lines 26 are arranged as shown in FIGS. 7 to 9.

At portions between the source coils 21A to 21C, identically to the signal lines 26A to 26L, the thermal radiating members 25 are wound along the core wire 23 with predetermined loose. This is the same reason as that in the case of winding the core wire 23 with predetermined loose.

Specifically, referring to FIGS. 2 and 3, the signal lines 26A and 26B and the thermal radiating members 25, which are wound to the core wire 23 between the source coils 21A to 21C arranged to the inserting portion bending portion 11a bent with the small curvature radius, are wound to the core wire 23 by five or six times with sufficient loose to the core wire 23. The signal lines 26A to 26L, which are wound to the core wire 23 between the source coils 21D to 21L arranged to the inserting portion flexible line portion 11b bent with the relatively large curvature radius, are wound to the core wire 23 by two or three times with some loose to the core wire 23.

Referring to FIG. 3, the thermal radiating members 25 are arranged at predetermined positions within the area reaching the outer circumference of the source coil 21A, the through-hole portion of the inner sheath 24S, the outer circumference of the source coil 21B, the through-hole portion of the inner sheath 24S, the outer circumference of the source coil 21C, and the through-hole portion of the inner sheath 24S, from the through-hole portion to the proximal end side of the inner sheath 24F arranged on the probe distal portion.

The number of signal lines 26 along the circumference of the source coil 21D and sequent ones is larger than the number of signal lines 26 along the circumference of the source coil 21A to 21C due to the signal lines 26 extended from the source coils 21A to 21C. As mentioned above, since the signal line 26 has the preferable thermal conductivity and therefore the signal line 26 has a function of the thermal radiating member without the thermal radiating member 25 for the source coils subsequent to the source coil 21D.

As the signal line 26 is nearer the proximal end side of the inserting shape detecting probe 1, the number of signal lines 26 is larger and the signal line 26 is thicker. Therefore, it is not preferable that the large number of thermal radiating members 25 is provided because of suppressing the outer diameter of the inserting shape detecting probe.

Therefore, according to the first embodiment, the thermal radiating members 25 are arranged to the source coils 21A to 21C as the first to third coils are arranged so as to sufficiently radiate the heat and to suppress the increase in outer diameter.

Referring to FIGS. 2 and 3, a tip piece 27 is arranged to the most front end portion of the outer sheath 20 in the inserting shape detecting probe 1.

According to the first embodiment, the outer portion of the outer sheath 20, the inner sheath 24, the outer coat of and the signal line 26 contain Teflon®. The characteristic that Teflon® is not fixed by adhesive is used and, upon the fixing operation with the adhesive, tetra-etching processing is performed so that the adhering surface is coarse as the pre-processing and the adhesive is sufficiently set.

When the thermal radiating members 25 contains an extra-fine metallic line which is the same as that of the signal line 26, the thermal radiating members 25 can be similarly handled and the assembling operation is easy. Further, the distinguishing operation is easy by changing the color of the outer portion of the thermal radiating members 25 from that of the signal line 26 and thus the operation is efficient.

Hereinbelow, a brief description is given of the procedure in assembling the inserting shape detecting probe 1 with the above-mentioned structure according to the first embodiment.

(1) The source coil 21A is inserted in the core wire 23 and further is adhered and fixed at a predetermined position. The six thermal radiating members 25 (hereinafter, the number of thermal radiating members is omitted) are extended to the distal end side from the source coil 21A, and are arranged on the back end side of the source coil 21A. Furthermore, the thermal radiating members 25 are arranged at a predetermined interval on the outer circumference of the source coil 21A in the state shown in FIG. 4.

(2) The inner sheath 24S is inserted in the core wire 23 and is arranged near the predetermined position. The signal line 26A extended from the source coil 21A and the thermal radiating members 25 are inserted in the inner sheath 24S.

(3) The inner sheath 24S is moved in the direction to the proximal end side, and the signal line 26A and the thermal radiating members 25 are wound to the core wire 23.

(4) After ending the winding operation of the signal line 26A and the thermal radiating members 25, the inner sheath 24S is returned to the predetermined position and is temporarily fixed. Then, the thermal contracting tube 40 covers a space between the source coil 21A and the inner sheath 24S, thereby integrally fixing the source coil 21A and the inner sheath 24S.

(5) The source coil 21B is inserted in the core wire 23 and is adhered and fixed at the predetermined position. The thermal radiating members 25 and the signal line 26A from the source coil 21A are arranged in the sate shown in FIG. 5. The thermal radiating members 25 are arranged toward the proximal end side.

(6) The inner sheath 24S is inserted in the core wire 23 and is arranged near the predetermined position. The signal line 26A guided from the inner sheath 24S, the signal line 26B extended from the source coil 21B, and the thermal radiating members 25 are inserted in the inner sheath 24S.

(7) The inner sheath 24S is moved on the proximal end side, and the signal lines 26A and 26B and the thermal radiating members 25 are wound to the core wire 23.

(8) After ending the winding of the signal lines 26A and 26B, the inner sheath 24S is returned at the predetermined position and is temporarily fixed. After that, the thermal contracting tube 40 covers a space between the source coil 21B and the inner sheath 24S, thereby integrally fixing the source coil 21B and the inner sheath 24S.

(9) The source coil 21C is inserted in the core wire 23 and is adhered and fixed at the predetermined position. The signal line 26A from the source coil 21A, the signal line 26B from the source coil 21B, and the thermal radiating members 25 are arranged in the state shown in FIG. 6. The thermal radiating members 25 are arranged toward the proximal end side.

(10) The inner sheath 24L is inserted in the core wire 23 and is arranged near the predetermined position. The signal lines 26A and 26B guided from the inner sheath 24S, the signal line 26C extended from the source coil 21C, and the thermal radiating members 25 are inserted in the inner sheath 24L.

(11) The inner sheath 24L is moved on the proximal end side, and the signal lines 26A to 26C and the thermal radiating members 25 are wound to the core wire 23. The thermal radiating members 25 are cut-off after ending winding operation of the wound portions.

(12) After ending the winding operation of the signal lines 26A to 26C, the inner sheath 24L is returned at the predetermined position and is temporarily fixed. After that, the thermal contracting tube 40 covers a space between the source coil 21C and the inner sheath 24L, thereby integrally fixing the source coil 21C and the inner sheath 24L.

In the subsequent procedure, the procedure excluding the thermal radiating members 25, that is, the procedure (1) to (12) is repeated and the source coil 21K and the inner sheath 24L are integrally fixed to the core wire 23.

(13) The inner sheath 24R is inserted in the core wire 23 and is arranged near the predetermined position. The signal lines 26A to 26L guided from the inner sheath 24L are inserted in the inner sheath 24R.

(14) The inner sheath 24R is moved on the proximal end side, and the signal liens 26A to 26L are wound to the endoscope 23.

(15) After ending the winding of the signal lines 26A to 26L, the inner sheath 24L is returned to the predetermined position and is temporarily fixed. After that, the thermal contracting tube 40 covers a space between the source coil 21L and the inner sheath 24R, thereby integrally fixing the source coil 21L and the inner sheath 24R.

(16) Finally, the distal end portions of the thermal radiating members 25 are in contact with the core wire 23 and are attached and fixed to the inner sheath 24 in accordance with the similar procedure.

(17) Herein, the signal lines 26A to 26L are subjected to the conductive test. If the conductive state of the signal lines 26A to 26L are confirmed, the outer sheath 20 is covered. In this case, the cover operation ends without the contact state of the outer sheath 20 and the signal lines 26A to 26L. Then, the tip piece 27 of the outer sheath 20 is arranged and thus the side of the distal end portion of the inserting shape detecting probe 1 is formed. The signal lines 26A to 26L extended from the outer sheath 20 are arranged at the predetermined positions of the connector portion 22, and thus the side of the proximal end portion of the inserting shape detecting probe 1 is formed.

Finally, it is inspected whether or not the shape of the inserting shape detecting probe 1 is displayed on the screen of the observing device. As a result, when the inspection is accepted, any means charges the air from the side of the connector portion 22, the final inspection is performed whether or not the damage of the pin hole exists in the outer sheath 20, and then the components is shipped.

The inserting shape detecting probe 1 is connected to the inserting shape detecting device shown in FIG. 1. The source coils 21 are driven by the driving signal from the inserting shape detecting device. Thus, the source coils 21 are heated and the heat in this case is radiated to the outside via the thermal radiating members 25 near the distal end portion of the inserting shape detecting probe 1. Further, near the proximal end portion rather than the portion where the thermal radiating members 25 are arranged, the heat is radiated to the outside via the signal line 26.

As described above, according to the first embodiment, the six thermal radiating members 25 are arranged along the outer circumference of the source coils 21A to 21C and the core wire 23 at the predetermined positions within the predetermined area (arrangement area of the source coils 21A to 21C from the distal end portion), from the predetermined portion on the distal end side of the inserting shape detecting probe 1 to the proximal end thereof. Thus, the temperature increase due to the heat generation of the source coils 21 are suppressed in the inserting shape detecting probe 1, particularly, near the distal end portion of the inserting shape detecting probe 1.

According to the first embodiment, the thermal radiating members 25 are arranged within the area between the first and third source coils, 21A and 21C. However, the present invention is not limited to the arrangement area of the thermal radiating members 25. The thermal radiating members 25 may be arranged within the area including at least one source coil, e.g., the outer circumference of the source coil 21A (shape detecting device) with high calorific-value, and the arrangement area of the thermal radiating members 25 may be set in accordance with the advantage of heat radiation.

According to the first embodiment, the description is given of the inserting shape detecting probe which is inserted in the treatment tool inserting channel of the endoscope. However, the present invention can be applied to an inserting shape detecting probe which is previously fixed in the inserting portion of the endoscope.

Further, according to the first embodiment, the number of thermal radiating members 25 is six. However, the number of thermal radiating members may be increased or decreased in accordance with the degree of the temperature increase.

Figure 10:
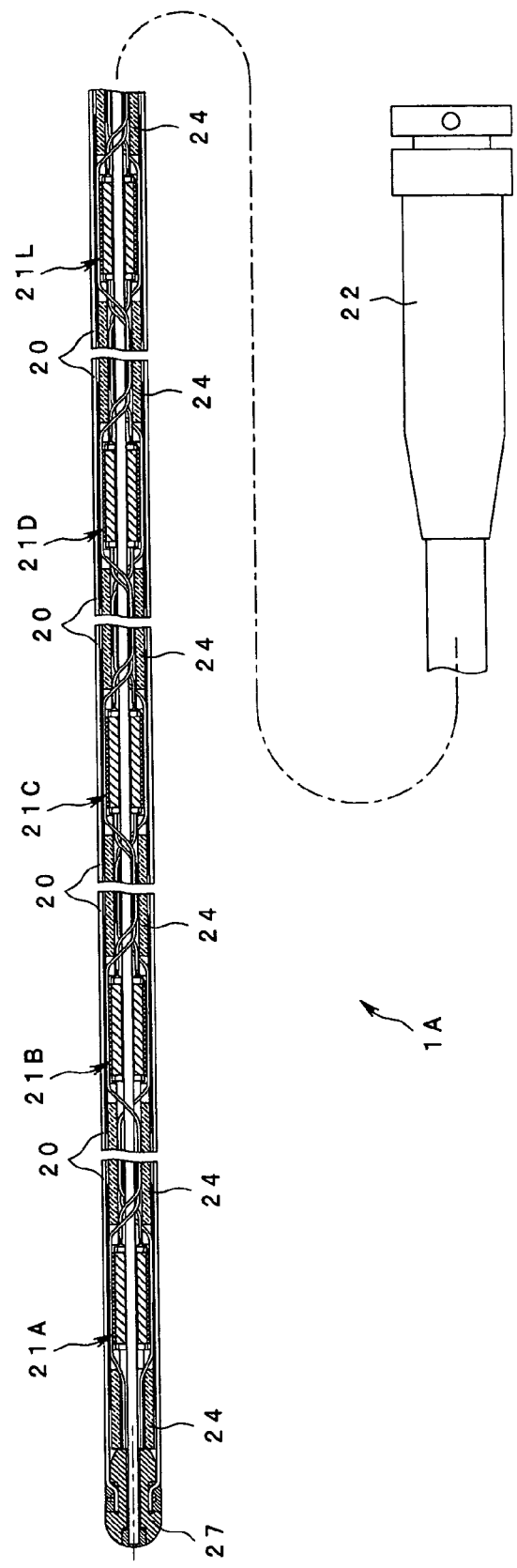
FIG. 10 is a cross-sectional view schematically showing the internal structure of an inserting shape detecting probe according to a second embodiment of the present invention.
Figure 11:
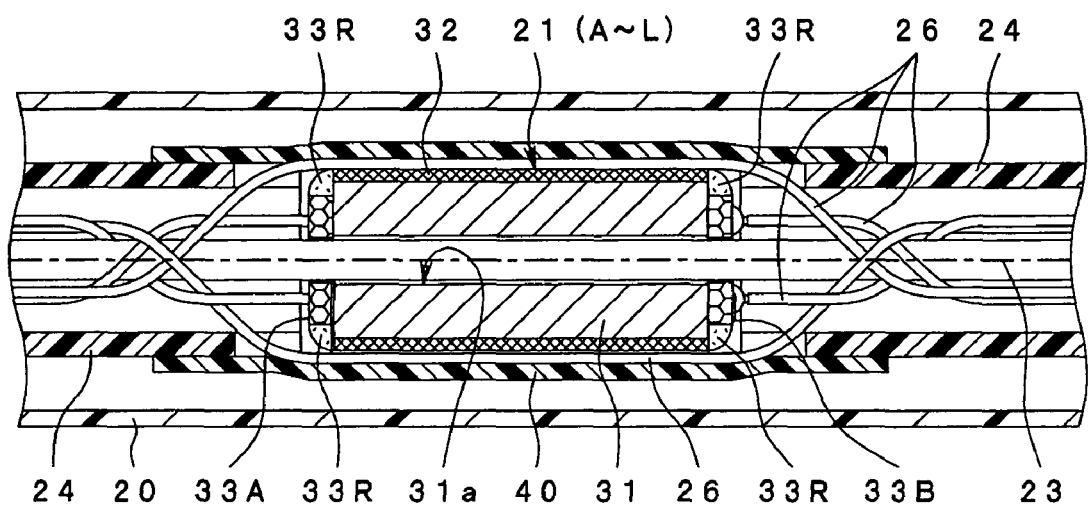
FIG. 11 is an enlarged cross-sectional view of a main portion showing a part of the inserting shape detecting probe shown in FIG. 10.

Next, a description is given of an inserting shape detecting probe according to a second embodiment with reference to FIGS. 10 and 11.

The basic structure according to the second embodiment is the same as that according to the first embodiment. Therefore, the same reference numerals denote the same components, a detailed description thereof is omitted, and only different portions are described. Further, the inserting shape detecting device using the inserting shape detecting probe according to the second embodiment is the same as that according to the first embodiment (refer to FIG. 1). Therefore, the schematic structure thereof is not described.

Hereinbelow, the detailed description is given of an inserting shape detecting probe 1A according to the second embodiment.

Referring to FIGS. 10 and 11, the inserting shape detecting probe 1A comprises: the outer sheath 20 which is inserted in the treatment tool inserting channel 15 and forms the exterior portion of the inserting shape detecting probe 1A; the source coils 21A to 21L which have hollow portions and are cylindrically formed; the long and slender core wire 23 to which the source coils 21A to 21L are adhered and fixed; the pipe-shaped inner sheaths 24 which are serially arranged to the source coils 21A to 21L; and the thermal contracting tube 40 which covers the source coils 21A to 21L and the inner sheaths 24 adjacent thereto, as a connecting and fixing member which integrally connects the source coils 21A to 21L and the inner sheaths 24.

Referring to FIG. 10, the source coils 21A to 21L and the inner sheath 24 are alternately arranged to the first source coil 21A, the inner sheath 24, the second source coil 21B, the inner sheath 24, the third source coil 21C, . . . , toward the proximal end portion from the distal end portion side of the inserting shape detecting probe 1A.

In the inserting shape detecting probe 1A according to the second embodiment, the number of the source coils is twelve. The source coil on the distal end side is the first source coil 21A, and the subsequent source coils are the second to twelfth source coils 21B to 21L.

The signal lines 26 are connected to one-end portions of the source coils 21A to 21L so as to transmit the driving signal from a source coil driving portion (not shown) of the inserting shape detecting device 7.

The source coils 21A to 21L fixed to the core wire 23 are arranged as follows. That is, the source coils 21A to 21C are arranged to the inserting portion bending portion 11a (refer to FIG. 1). In this case, the source coils 21A to 21C function as devices for detecting the shape of the bending portion, which obtain the shape data of the inserting portion bending portion 11a. Further, the source coils 21D to 21L are arranged to the inserting portion flexible line portion 11b (refer to FIG. 1). In this case, the source coils 21D to 21L function as devices for detecting the shape of the bending portion, which obtain the shape data of the inserting portion flexible line portion 11b.

The signal lines 26 connected to the source coils 21A to 21L are inserted in the inner sheaths 24 arranged at the proximal end portions of the source coils 21A to 21L and are extended to the proximal end side. That is, the signal line 26 extended from the source coil 21A is inserted in the outer sheath 20 along the side peripheral surfaces of the entire source coils 21B to 21L as the source coils including one adjacent to the source coil 21A to the final one, and are finally extended to the connector portion 22 on the proximal end side of the inserting shape detecting probe 1A. Therefore, as the inner sheath 24 is near the proximal end of the inserting shape detecting probe 1A, the larger number of signal lines 26 is inserted.

The signal lines 26 inserted in the inner sheath 24 are wound along the core wire 23 with predetermined loose. Because the tension is applied to the signal lines 26 upon bending the inserting shape detecting probe 1A and then the damage such as short circuit is prevented.

The source coils 21A to 21L are fixed to the core wire 23 with an adhesive or the like at a predetermined interval. Referring to FIG. 11, the source coils 21A to 21L mainly comprise: the hollow core member 31 having the through-hole 31a, which is pierced in the axial direction; the winding 32 which is wound to the hollow core member 31 and contains an enamel line or the like; and donut-shaped substrates 33A and 33B which are arranged on both end surfaces of the hollow core member 31.

The substrates 33A and 33B are adhered and fixed to both end surfaces of the source coils 21. Referring to FIG. 11, the peripheral portions of the substrates 33A and 33B are subjected to the R-chamfer. The portion subjected to the R-chamfer is referred to an R-chamfered portion, and is designated by reference symbol 33R in FIG. 11.

Among the substrates 33A and 33B, both end portions of the winding 32 are electrically connected to the substrate 33B by soldering. Further, the signal lines 26 are electrically connected to the substrate 33B by means such as soldering.

The tip piece 27 is arranged to the most front end portion of the outer sheath 20 in the inserting shape detecting probe 1A.

According to the second embodiment, the outer portion of the outer sheath 20, the inner sheath 24, and the outer coat of the signal line 26 contains Teflon®. The characteristic that Teflon® is not fixed by adhesive is used and, upon the fixing operation with the adhesive, tetra-etching processing is performed so that the adhering surface is coarse as the pre-processing and the adhesive is sufficiently set.

Hereinbelow, a brief description is given of the procedure in assembling the inserting shape detecting probe 1A with the above-mentioned structure according to the second embodiment.

(1) The source coil 21A is inserted in the core wire 23 and further is adhered and fixed at a predetermined position thereof.

(2) The inner sheath 24 is inserted in the core wire 23 and is arranged near the predetermined position thereof. The signal line 26 extended from the source coil 21A is inserted in the inner sheath 24.

(3) The inner sheath 24 is moved in the direction on the proximal end side, and the signal line 26 is wound to the core wire 23.

(4) After ending the winding operation of the signal line 26, the inner sheath 24 is returned to the predetermined position and is temporarily fixed. Then, the thermal contracting tube 40 covers a space between the source coil 21A and the inner sheath 24, thereby integrally fixing the source coil 21A and the inner sheath 24.

(5) The source coil 21B is inserted in the core wire 23 and is adhered and fixed at the predetermined position thereof. The signal line 26 from the source coil 21A is arranged at the predetermined position on the outer circumference of the source coil 21B.

(6) The next inner sheath 24 (hereinafter, referred to as a second inner sheath 24) is inserted in the core wire 23 and is arranged near the predetermined position. The signal line 26 which is guided from the inner sheath 24 and fixed to the core wire 23 in the procedure (2) and the signal line 26 extended from the source coil 21B are inserted in the second inner sheath 24.

(7) The second inner sheath 24 is moved on the proximal end side, and the two signal lines 26 are wound to the core wire 23.

(8) After ending the winding of the two signal lines 26, the second inner sheath 24 is returned at the predetermined position and is temporarily fixed. After that, the thermal contracting tube 40 covers a space between the source coil 21B and the second inner sheath 24, thereby integrally fixing the source coil 21B and the second inner sheath 24.

The procedure (1) to (8) is repeated, thus to integrally fix, to the core wire 23, the source coil 21C, the inner sheath 24, . . . , the source coil 21L, and the inner sheath 24 as the most back end portion.

(9) Herein, the signal lines 26 are subjected to the conductive test. If the conductive state of the signal lines 26 are confirmed, the outer sheath 20 is covered. In this case, the cover operation ends without the contact state of the outer sheath 20 and the signal line 26.

(10) Then, the tip piece 27 of the outer sheath 20 is arranged and thus the side of the distal end portion of the inserting shape detecting probe 1A is formed. The signal lines 26 extended from the outer sheath 20 are arranged at the predetermined positions of the connector portion 22, and thus the side of the proximal end portion of the inserting shape detecting probe 1A is formed.

(11) Finally, it is inspected whether or not the shape of the inserting shape detecting probe 1A is displayed on the screen of the observing device. As a result, when the inspection is accepted, any means charges the air from the side of the connector portion 22, the final inspection is performed whether or not the damage of the pin hole exists in the outer sheath 20, and then the components is shipped.

As mentioned above, according to the second embodiment, the substrates 33A and 33B having the peripheral portions as the R-chamfered portions 33R are fixed to both the end surfaces of the source coils 21A to 21L as the plurality of shape detecting devices. Thus, when any load is applied to the signal lines 26 in the assembling process or upon using the inserting shape detecting probe 1A, the signal lines 26 are in contact with the R-chamfered portion 33R therealong. In this case, the load applied to the R-chamfered portion 33R is distributed depending on the shape. This suppresses the overload to the windings 32 of the source coils 21A to 21L and the signal lines 26, and the peeling of the covers on the coils is prevented.

With the excessively simple structure that only the R-chamfered portions 33R are arranged to the peripheral portions of both the end surfaces of the source coils 21A to 21L, the damage of members such as the signal lines 26 or the windings 32 of the source coils 21A to 21L caused in the assembling process is prevented without fail. Further, the yield is improved and this contributes to the improvement of productivity. Since it is possible to suppress the peeling of covers of coils in the bending operation, the resistant property is improved.

According to the second embodiment, the substrates 33A and 33B having the R-chamfered portions 33R at the peripheral portions thereof are fixed to both the ends of the source coils 21A to 21L. However, the present invention is not limited to this. For example, a C-chamfered portion may be formed to the substrates 33A and 33B, in place of the R-chamfered portion 33R near the peripheral portions of the substrates 33A and 33B. Unlike the second embodiment, in this case, only the shape of the chamfered portion is different.

Further, a substrate with the diameter slightly smaller than those of the source coils 21A to 21L is adhered and fixed to both the ends of the source coils 21A to 21L, and a resin member such as an adhesive having the elasticity in the rigid state at the uneven portion and therefore the chamfered portion may be formed similarly to the R- or C-chamfered portion.

Furthermore, in place the substrates 33A and 33B having the R- or C-chamfered portion, by fixing the resin member such as the adhesive with the elasticity upon fixing, near the peripheral portion of both ends of the source coils 21A to 21L, the chamfered portion may be formed similarly to the R- or C-chamfered portion. When various-shaped chamfered portion or the shape thereof is formed near the peripheral portion of both the ends of the source coils, the same advantages as those according to the second embodiment are obtained.

The inserting shape detecting probe 1A may be built-in and fixed to the inserting portion of the endoscope as well as the inserting shape detecting probe 1A which is inserted in the treatment tool inserting channel of the endoscope apparatus.

Figure 15:
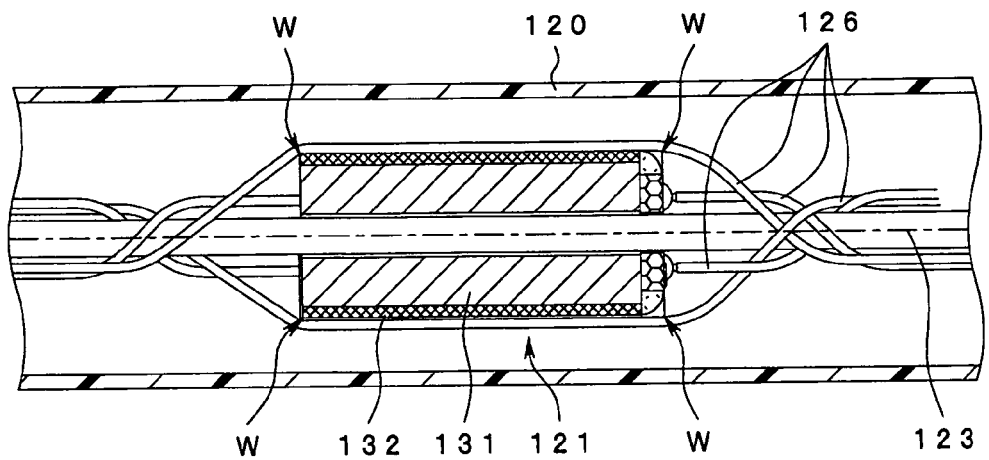
FIG. 15 is an enlarged cross-sectional view of a main portion showing a part of one conventional inserting shape detecting probe.
Figure 17:
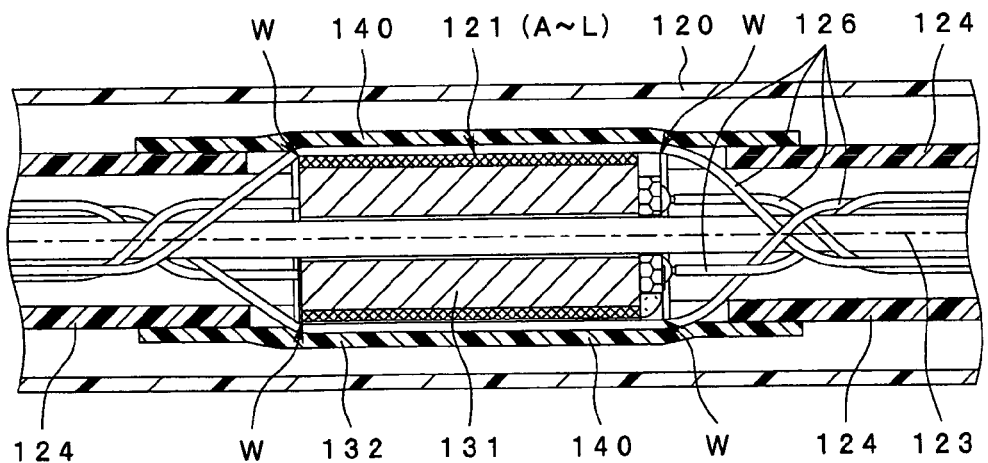
FIG. 17 is an enlarged cross-sectional view of a main portion showing a part of the other inserting shape detecting probe shown in FIG. 16.
Figure 16:
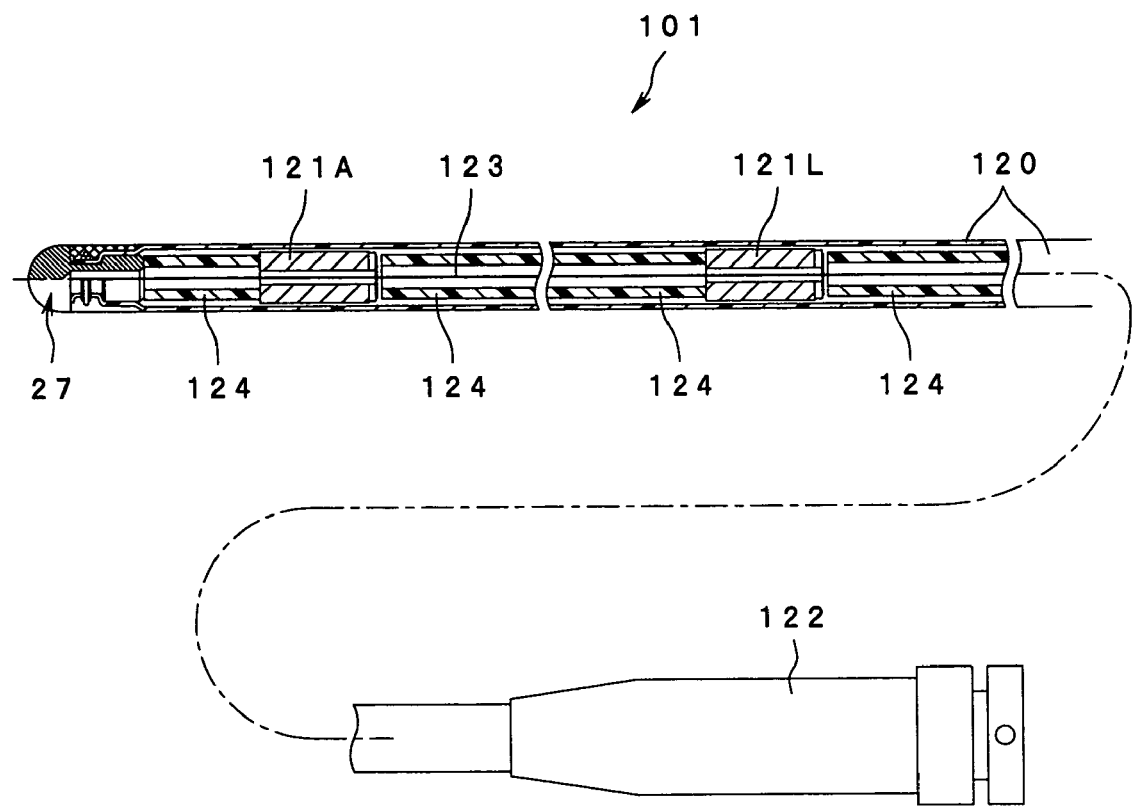
FIG. 16 is a diagram showing the entire structure of another conventional inserting shape detecting probe.

In the conventional inserting shape detecting probe shown in FIGS. 15 to 17, a predetermined electric substrate for ensuring the conductivity to the source coil is fixed to one end surface on the side of the proximal end portions of each source coil, and the signal line is extended via the electric substrate.

Figure 18:
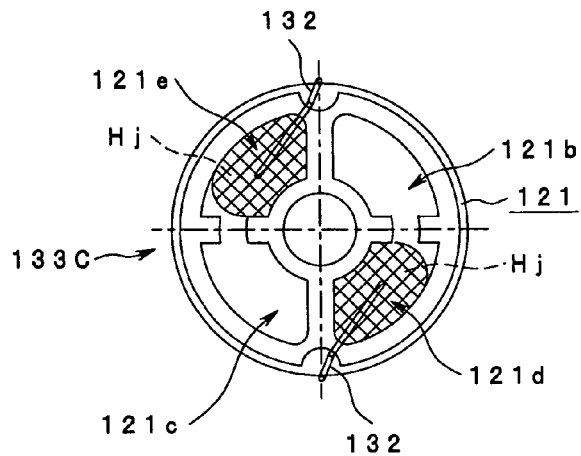
FIG. 18 is a plan view showing an electric substrate arranged to one end surface (proximal end side) of a source coil used for the conventional inserting shape detecting probes, when a winding of the source coil is soldered to a second land of the electric substrate.
Figure 19:
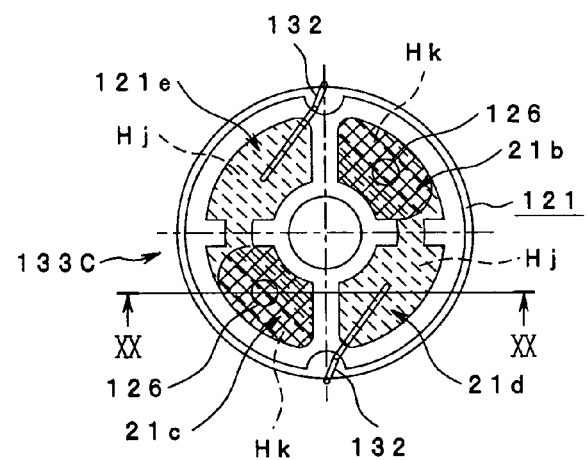
FIG. 19 is a plan view showing a state in which the signal line is soldered to a first land in addition to the state shown in FIG. 18.
Figure 20:
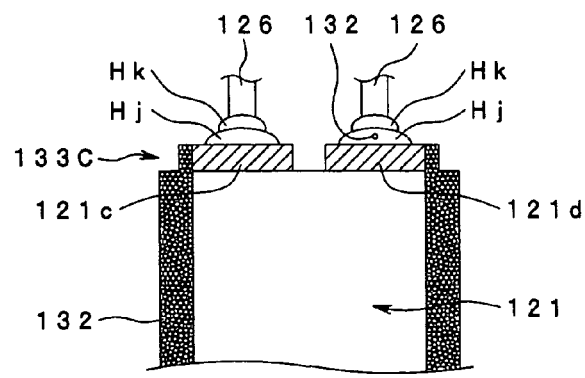
FIG. 20 is a cross-sectional view along a XX-XX line in FIG. 19, when the signal line is soldered to the first land of the electric substrate.

FIGS. 18 to 20 are diagrams showing the electric substrate arranged to the one end surface of the source coil (on the proximal end side thereof). FIG. 18 is a plan view showing a state in which the coil of the source coil is soldered to a second land of the electric substrate. FIG. 19 is a plan view showing a state in which the signal line is soldered to a first land in addition to the state shown in FIG. 18. FIG. 20 is a cross-sectional view along a XX-XX line shown in FIG. 19, showing a state in which the signal line is soldered to the first land of the electric substrate.

As mentioned above, an electric substrate 133C is fixed to the one end surface of a source coil 121 with the adhesive or the like. Referring to FIGS. 18 and 19, the electric substrate 133C comprises: first lands 121b and 121c and second lands 121d and 121e. Further, the first land 121b is electrically connected to the second land 121d, thereby forming one connecting pole. Furthermore, the first land 121c is electrically connected to the second land 121e, thereby forming another connecting pole. Thus, a pair of connecting poles is formed.

The one connecting pole comprising the first land 121b and the second land 121d is electrically connected to the other connecting pole between the first land 121c and the second land 121e.

Both ends of a winding 132 of the source coil 121 and two signal lines 126 are fixed and connected to the electric substrate 133 by soldering as follows.

That is, both ends of the winding 132 of the source coil 121 are soldered to the second lands 121d and 121e of the electric substrate 133C at the high temperature. Thus, a high-temperature-soldering layer Hj is formed on the second lands 121d and 121e. The soldering at the high temperature might passes through a path 128 arranged to a partition for partitioning the first lands 121b and 121c and the second lands 121d and 121e, and might thus flow out to the first lands 121b and 121c from the second lands 121d and 121e.

Next, the two signal lines 126 are soldered to the first lands 121b and 121c at the low temperature. In this case, the high-temperature soldering layer Hj has already been formed on the first lands 121b and 121c and therefore a low-temperature soldering layer Hk is formed on the high-temperature soldering layer Hj.

Referring to FIG. 20, the two signal lines 26 are connected and fixed to the first lands 121b and 121c. Both ends of the winding 132 of the source coil 121 are connected to the second lands 121d and 121e. Further, the first land 121b and second land 121d are connected to the first land 121c and second land 121e via the high-temperature soldering layer Hj.

With the structure, the high-temperature soldering flows in the first lands 121b and 121c. In this case, the low-temperature soldering layer Hk is formed onto the flowed-in high-temperature soldering layer Hj and, at this position, the signal line 126 is connected and fixed. Upon soldering the signal lines 126 at the low temperature, the portion of the high-temperature soldering layer Hj formed to the bottom layer is not soldered. Therefore, the high-temperature soldering layer Hj is not fused to the low-temperature soldering layer Hk. The high-temperature soldering layer Hj and the low-temperature soldering layer Hk are laminated. Only the weak adhering force acts to both the high-temperature soldering layer Hj and the low-temperature soldering layer Hk. Upon applying any external force to the low-temperature soldering layer Hk, the low-temperature soldering layer Hk is peeled and thus the signal lines 126 are detached form the source coils 121.

Figure 12:
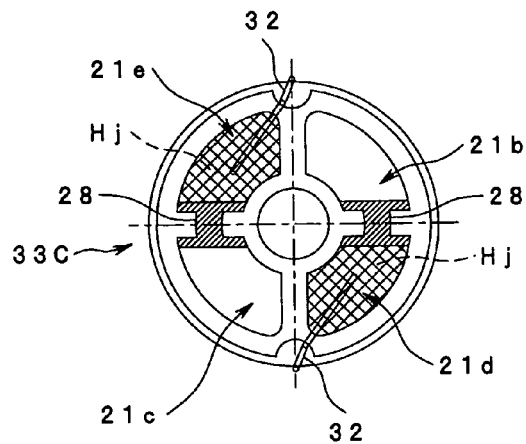
FIG. 12 is a plan view showing an electric substrate arranged to one end surface of a shape detecting device (source coil) used for the inserting shape detecting probe according to the second embodiment, when the winding of the shape detecting device (source coil) is soldered to a second land of the electric substrate.
Figure 13:
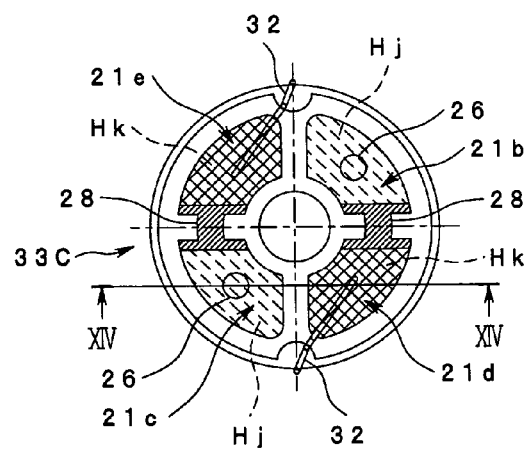
FIG. 13 is a plan view showing a state in which a signal line is soldered to a first land in addition to the state shown in FIG. 12.
Figure 14:
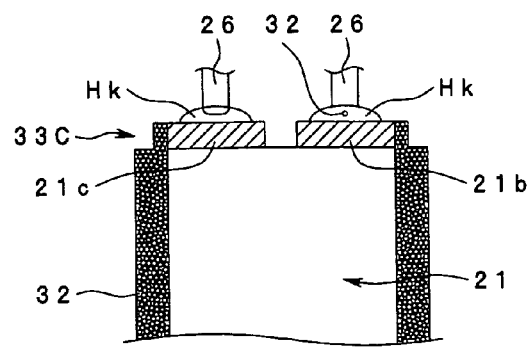
FIG. 14 is a cross-sectional view along a XIV-XIV line shown in FIG. 13, when the signal line is soldered to the first land of the electric substrate.

Then, a description is given of the electric substrate on which the winding of the source coil is certainly connected and fixed to the signal line with reference to FIGS. 12 to 14.

Referring to FIGS. 12 and 13, a substrate 33C of the source coil 21 as the shape detecting device comprises: first lands 21b and 21c and second lands 21d and 21e. The first land 21b is electrically connected to the second lands 21d, thereby forming one connecting pole. The first land 21c is electrically connected to the second lands 21e, thereby forming another connecting pole. Thus, a pair of connecting poles is formed.

The one connecting pole comprising the first land 21b and the second land 21d is electrically connected to the other connecting pole between the first land 21c and the second land 21e.

On the substrate 33C, the first land 21b is electrically connected to the second lands 21d, thereby forming a pattern. A partitioning member 28 is formed so as to form a partitioning portion for partitioning the first land 21b and the second lands 21d and a portioning portion for partitioning the first land 21c and the second lands 21e. The partitioning member 28 may contain any member resistant to the temperature in the soldering operation.

Both ends of the winding 32 of the source coil 21 and the two signal lines 26 are connected and fixed to the substrate 33C with the above-mentioned structure by soldering.

That is, both the ends of the winding 32 of the source coil 21 are soldered to the second lands 21d and 21e in the substrate 33C with high temperature. The high-temperature soldering in this case does not flow to the first lands 21b and 21c by the partitioning member 28 and forms the high-temperature soldering layer Hj only on the second lands 21d and the second lands 21e. Then, the winding 32 is connected and fixed to the high-temperature soldering layer Hj.

Next, the two signal lines 26 are soldered to the first lands 21b and 21c at the low temperature. Thus, the low-temperature soldering layer Hk is formed to the first lands 21b and 21c.

Referring to FIG. 14, only the low-temperature soldering layer Hk is formed on the first lands 21b and 21c on the substrate 33C, and the signal lines 26 are connected and fixed to the low-temperature soldering layer Hk.

As described above, by arranging only the partitioning member 28 to the substrate 33C, the first lands 21b and 21c to which the signal lines 26 are connected and fixed are electrically connected to the second lands 21d and 21e to which the winding 32 of the source coil 21 is connected and fixed. Further, the high-temperature soldering layer Hj is certainly partitioned from the low-temperature soldering layer Hk.

Therefore, the predetermined signal line 26 or winding 32 is connected and fixed to the respective lands 21b to 21e.

It should be understood that the present invention is not limited to those embodiments and various changes and modifications thereof could be made without departing from the spirit of scope of the invention as defined in the appended claims.

What is claimed is:

1. An inserting shape detecting probe having a long and slender core wire, a plurality of inner sheaths, a connecting and fixing member, and an outer sheath, the core wire having a plurality of shape detecting devices fixed thereto at a predetermined interval, the plurality of shape detecting devices having signal lines extended therefrom, at least one of the inner sheaths having a through-hole pierced therethrough in an axial direction for inserting therein the signal lines extended from the plurality of shape detecting devices, the inner sheaths being arranged at portions where the shape detecting devices are not arranged on the core wire, the connecting and fixing member being arranged between at least one of the shape detecting devices and at least one of the inner sheaths adjacent thereto and integrally connecting the shape detecting device and the inner sheath, the outer sheath having the shape detecting devices and the inner sheaths inserted therein, the inserting shape detecting probe comprising:

a thermal radiating member being extended in the axial direction of the inserting shape detecting probe along the outer circumference of at least one of the shape detecting devices including at least the distal-most of the shape detecting devices, the thermal radiating member having a portion that is inserted in at least one of the inner sheaths and that is arranged along an outer circumferential surface of the core wire, the thermal radiating member being extended in an axial direction of the outer sheath and arranged between the outer circumferential surface of the core wire and an inner surface of the through-hole of at least one of the inner sheaths, the thermal radiating member being wound along the outer circumferential surface of the core wire so as to generate looseness.

2. An inserting shape detecting probe according to claim 1, wherein the thermal radiating member is inserted in the connecting and fixing member.

3. An inserting shape detecting probe according to claim 1, wherein at least one of the shape detecting devices is a coil.

4. An inserting shape detecting probe according to claim 1, further comprising a plurality of the thermal radiating members.

5. An inserting shape detecting probe according to claim 1, wherein the thermal radiating member contains a highly-conductive material.

6. An inserting shape detecting probe according to claim 5, wherein the thermal radiating member is a metallic line.

7. An inserting shape detecting probe according to claim 5, wherein the signal lines contains the same material as that of the thermal radiating member.

8. An inserting shape detecting probe according to claim 7, wherein the color of the outer coat of the thermal radiating member is different from that of the signal lines.

\* \* \* \* \*